United States Patent [19]

Carter et al.

[11] 4,406,868
[45] Sep. 27, 1983

[54] PROCESS AND APPARATUS FOR REMOVING H₂S FROM GAS STREAMS

[75] Inventors: Cecil O. Carter, Wann; Dwight D Boesiger, Bartlesville, both of Okla.

[73] Assignee: Phillips Petroleum Company, Bartlesville, Okla.

[21] Appl. No.: 321,017

[22] Filed: Nov. 13, 1981

[51] Int. Cl.³ .......................................... B01D 53/34
[52] U.S. Cl. .................................. 423/228; 423/226; 423/229
[58] Field of Search ...................... 423/226, 228, 229

[56] References Cited

U.S. PATENT DOCUMENTS

| | | | |
|---|---|---|---|
| 3,139,324 | 6/1964 | Housset | 23/2 |
| 3,622,267 | 11/1971 | Bartholome et al. | 23/2 R |
| 3,696,162 | 10/1972 | Kniel | 260/677 A |
| 3,962,404 | 6/1976 | Giammarco et al. | 423/222 |
| 3,965,244 | 6/1976 | Sykes, Jr. | 423/228 |
| 3,989,811 | 11/1976 | Hill | 423/573 G |
| 4,073,863 | 2/1978 | Giammarco et al. | 423/222 |
| 4,085,192 | 4/1978 | Van Scoy | 423/226 |
| 4,093,701 | 6/1978 | Butwell | 423/228 |
| 4,289,738 | 9/1981 | Pearce et al. | 423/228 |

OTHER PUBLICATIONS

Pearce, "Hydrogen Sulfide Removal with Methyl Diethanolamine", Gas Processors Association, Proc. of the 57th Annual Conv., New Orleans, 3/78.
Blanc et al., "MDEA Process Selects H₂S" Hydrocarbon Processing, 8/81, p. 111.
Frazier et al., "Selective Absorption of Hydrogen Sulfide from Gas Streams, " 42 #11 Ind. & Eng. Chem., 11/50, p. 2228.
Miller et al., "Selective Absorption of Hydrogen Sulfide" 51 #51 Oil & Gas J. 4/27/53, p. 175.
Vidaurri et al., "Recover H₂S Selectively from Sour Gas Streams," Hydrocarbon Processing, 11/77, p. 333.

*Primary Examiner*—O. R. Vertiz
*Assistant Examiner*—Jackson Leeds

[57] ABSTRACT

A gas stream containing $CO_2$ and $H_2S$ is contacted with an alkanolamine in a contacting zone. The rich solution is then selectively stripped in a stripping zone to produce a gas stream containing a higher $CO_2$:$H_2S$ mole ratio than the initial stream. This stream can be recycled to the alkanolamine contacting zone. The partially stripped solution can be introduced into another stripping zone to provide a third gas stream which is rich in $H_2S$ and lean in $CO_2$ suitable as feed for a Claus Unit and a lean alkanolamine solution which can be recycled to the contacting zone.

16 Claims, 1 Drawing Figure

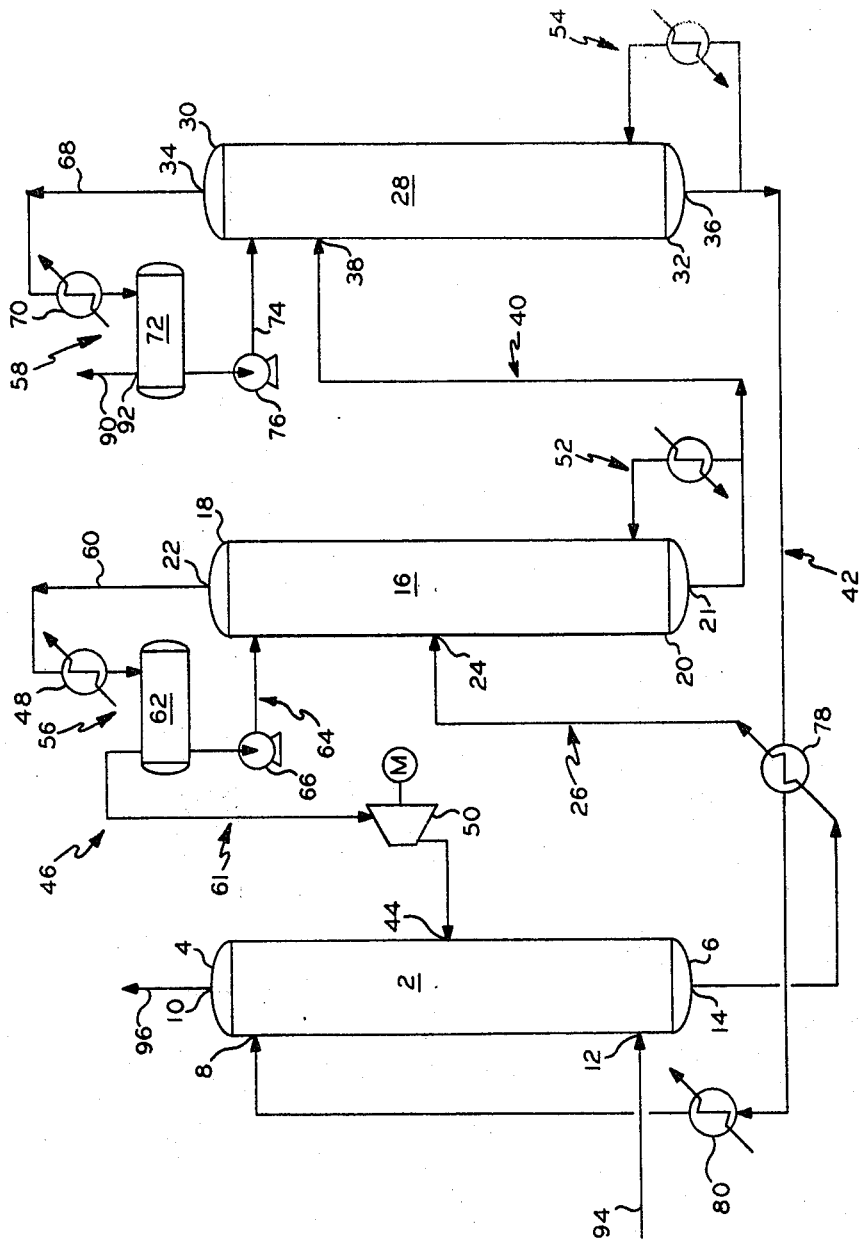

4,406,868

PROCESS AND APPARATUS FOR REMOVING H₂S FROM GAS STREAMS

BACKGROUND OF THE INVENTION

The invention relates to the treatment of gas streams. In another aspect the invention relates to treating an acid gas stream with an alkanolamine solution. In yet another aspect, the invention relates to selectively regenerating alkanolamine solution which has been contacted with acid gases.

The use of amines for the removal of hydrogen sulfide and carbon dioxide from gas streams is well known. Triethanol amine (TEA) was the first of the ethanol amines to become commercially available. It was used in the early gas treating plants. This amine has generally been displaced in gas treating plants by diethanol amine (DEA) and monoethanol amine (MEA). The advantage to the use of DEA and MEA lies in their lower molecular weights and their ability to more completely absorb hydrogen sulfide from the gas. Of these three amines, monoethanol amine is generally preferred because of its ability to produce sweet gas streams with extremely low hydrogen sulfide levels under the same operating conditions.

Frequently, large quantities of carbon dioxide occur in gas streams containing hydrogen sulfide. When complete hydrogen sulfide removal is attained, processes utilizing MEA and DEA also absorb essentially all of the carbon dioxide. There are frequent occasions when it would be desirable to send a major portion of the carbon dioxide with the treated gas stream while removing essentially all of the hydrogen sulfide. The current need for processes to selectively remove hydrogen sulfide from gas streams can be summarized as follows:

(1) The high cost of energy required to regenerate the amine solution can be reduced if less carbon dioxide is absorbed.
(2) The Claus process requires a high ratio of hydrogen sulfide to carbon dioxide for most economic operation, otherwise capital and operating costs for a Claus plant could soar.
(3) As environmental restrictions become more stringent, many of the low hydrogen sulfide to carbon dioxide streams now being flared will have to be treated before flaring.
(4) Synthetic natural gas streams are very high in carbon dioxide and must be de-sulfurized before feeding to any known catalytic conversion process to produce high BTU fuel.

OBJECTS OF THE INVENTION

It is an object of this invention to selectively remove H₂S from gas streams also containing CO₂.

It is another object of this invention to provide a process which can be utilized to prepare feed for a Claus plant so that H₂S can be converted to sulfur.

It is another object of the invention to provide a process for treating gas streams containing a low $H_2S:CO_2$ mole ratio.

It is yet another object of this invention to provide a low-pressure process for the production of high purity $H_2S$.

It is yet another object of the invention to provide a process which can be employed to de-sulfurize synthetic natural gas streams rich in carbon dioxide.

SUMMARY OF THE INVENTION

According to one embodiment of the present invention, an apparatus comprises a first column having an upper end and a lower end with a liquid inlet and vapor outlet adjacent its upper end and a vapor inlet and liquid outlet adjacent its lower end; a second column having an upper end and a lower end with a vapor outlet adjacent its upper end, a liquid outlet adjacent its lower end, and a liquid inlet between its upper end and its lower end; a first conduit means connecting the liquid outlet adjacent the lower end of the first column with a liquid inlet between the upper end and the lower end of the second columns; a third column having an upper end and a lower end with a vapor outlet adjacent its upper end, a liquid outlet adjacent its lower end, and a liquid inlet between its upper end and its lower end; a second conduit means connecting the liquid outlet adjacent the lower end of the second column with the liquid inlet between the upper end and the lower end of the third column; and a third conduit means connecting the liquid outlet adjacent the lower end of the third column with the liquid inlet adjacent the upper end of the first column. Desirably, the first column serves as an alkanolamine contacting zone, the second column serves as a selective stripping zone for producing an overhead stream relatively rich in $CO_2$ which can be recycled to the contacting zone and a bottoms stream which is relatively rich in $H_2S$ and can be conveyed to the third column. The third column can serve to substantially regenerate the alkanolamine solution, producing an overhead stream rich in $H_2S$ and lean in $CO_2$ suitable for feed to a Claus unit, or to another unit for the production of high-purity, e.g. greater than 99 mole %, $H_2S$, and a bottoms stream comprising lean alkanolamine solution which can be recycled to the contacting zone.

According to another aspect of the present invention, a process comprises contacting a first gas stream containing $CO_2$, $H_2S$ and at least one hydrocarbon with a solution of at least one alkanolamine in a contacting zone; withdrawing a rich solution of at least one alkanolamine from the contacting zone which is rich in $H_2S$ and $CO_2$ from the first gas stream; introducing the rich solution into a separation zone; selectively stripping the rich solution in the separation zone to produce a second gas stream issuing from the separation zone which contains a higher $CO_2:H_2S$ mole ratio than the first stream; and conveying the second gas stream into an alkanolamine contacting zone which can be the same as or different from the first zone. By conveying the second stream to the alkanolamine contacting zone, a greater portion of the $CO_2$ contained in the first gas stream can be slipped and still meet $H_2S$ removal requirements for the treated stream. By selectively stripping the rich solution in the separation zone, a partially stripped solution can be obtained with contains a higher $H_2S:CO_2$ mole ratio than the rich solution from the contacting zone.

In accordance with yet another aspect of the present invention, a process comprises contacting a first gas stream containing $H_2S$, $CO_2$ and at least one hydrocarbon with a lean alkanolamine solution in a contacting zone; withdrawing a rich alkanolamine solution from the contacting zone which contains at least a portion of the $H_2S$ and $CO_2$ from the first gas stream; introducing the rich alkanolamine solution into a first stripping zone; selectively stripping the rich alkanol solution in the first stripping zone to produce a second gas stream issuing from the stripping zone which contains a higher $CO_2:H_2S$ mole ratio than the first gas stream; withdrawing a selectively stripped alkanolamine solution from the first stripping zone; said selectively stripped alkanolamine solution containing a higher $H_2S:CO_2$ mole ratio than the rich alkanolamine solution from the contacting zone; introducing the selectively stripped solution into a second stripping zone; and stripping the selectively stripped solution to produce a third gas stream which is rich in $H_2S$ and lean in $CO_2$. By utilizing two stripping zones, a third gas stream can be obtained which can be desirably processed in a Claus unit, due to its high $H_2S:CO_2$ mole ratio. If desired, the second gas stream can be recycled to the contacting zone for removal of residual $H_2S$ and additional slippage of $CO_2$.

BRIEF DESCRIPTION OF THE DRAWING

The FIGURE illustrates schematically certain features of the present invention.

DETAILED DESCRIPTION OF THE INVENTION

According to the invention, a treating vessel such as a column 2 has an upper end 4 and lower end 6. A liquid inlet 8 and a vapor outlet 10 open into the column 2 adjacent its upper end 4 and a vapor inlet 12 and a liquid outlet 14 open into the column 2 adjacent its lower end 6. A second column 16 having an upper end 18 and lower end 20 is provided with a liquid outlet 21 adjacent its lower end, a vapor outlet 22 adjacent its upper end and a liquid inlet 24 between its upper end 18 and its lower end 20. A first conduit means 26 connects the liquid outlet 14 adjacent the lower end 6 of the first column 2 with the liquid inlet 24 between the upper end 18 and the lower end 20 of the second column 16. A third column 28 having an upper end 30 and a lower end 32 is provided with a vapor outlet 34 adjacent its upper end 30, a liquid outlet 36 adjacent its lower end 32 and a liquid inlet 38 between its upper end 30 and its lower end 32. A second conduit means 40 connects the liquid outlet 21 adjacent the lower end 20 of the second column 16 with the liquid inlet 38 between the upper end 30 and the lower end 32 of the third column 28. A third conduit means 42 connects the liquid outlet 36 adjacent the lower end 32 of the third column 28 with the liquid inlet 8 adjacent the upper end 4 of the first column 2.

Preferably, the first column 2 is further provided with a second vapor inlet 44 between its upper end 4 and its lower end 6. A fourth conduit means 46 connects the vapor outlet 22 adjacent the upper end 18 of the second column 16 with the second vapor inlet 44 opening into the first column 2 between its upper end 4 and its lower end 6.

A reboiler means 52 is operably connected to the lower end 20 of the second column 16, while a reboiler means 54 is operably connected to the lower end 32 of the third column 28. Preferably, the reboilers 52 and 54 are of the thermosiphon type. Preferably, the second column 16 and the third column 28 are provided with a means 56 and 58 respectively for returning reflux to the upper portions of the columns. From the vapor outlet 22 in the upper portion 18 of the column 16, there extends a conduit 60 which, after passing into operable association with a condensor 48, empties into a reflux accumulator 62. A conduit means 64 establishes a flow path from a lower portion of the accumulator 62 to the upper portion 18 of the column 16. A pump 66 is associated with the conduit 64 for causing liquid flow from the accumulator 62 to the upper portion of the column 18. A conduit means 61 establishes a flow path from an upper portion of the accumulator 62 to the inlet 44 of the column 2. A compressor 50 is associated with the conduit 61 for causing vapor flow from the upper portion of the accumulator to the inlet 44 of the column 2. The means 46 preferably comprises the conduit 60, condensor 48, accumulator 62, conduit 61, and compressor 50. A conduit 68 extends from the vapor outlet 34 in the upper portion 30 of the third column 28 and, after passage through a condensor 70 empties into an accumulator 72. A conduit 74 establishes a flow path between a lower portion of the accumulator 72 and the upper portion 30 of the third column 28. A pump 76 is operably connected to the conduit 74 for causing liquid flow from the accumulator 72 to the upper portion 30 of the column 28.

It is preferred that at least one heat exchange means be associated with the conduit means 42 for cooling fluid flow therethrough. In the illustrated embodiment, a portion of the conduit means 26 passes in heat exchange relationship with the conduit means 42 at heat exchanger 78. A cooler 80 is further disposed in the conduit 42 between the heat exchanger 78 and the liquid inlet 8 in the upper portion 4 of the column 2 for cooling liquid flow through the conduit means 42 to a desired temperature.

A conduit 90 connected to a vapor outlet 92 in an upper portion of the accumulator 72 can be connected to a Claus unit, not shown, if desired. A conduit 94 is connected to the vapor inlet in the lower portion 6 of the column 2, and will usually be connected to a pipeline system or a cracking zone not shown. Treated desulfurized gas is withdrawn from the zone 2 via 96 and is utilized as desired.

To help eliminate corrosion problems, the unit can be constructed of a suitable corrosion-resistant material, such as 304 stainless steel. The column 2 can be an absorber fitted with sieve trays, liquid downcomers and overflow weirs. The columns 16 and 28 can be packed with a suitable material to increase available surface area, such as ⅜" stainless steel Pall rings.

In operation, a gas stream 94 containing $CO_2$, $H_2S$, and at least one hydrocarbon is contacted with a solution of at least one alkanolamine in a contacting zone 2, usually an absorber. The first gas stream could have its origin, for example, in a sour natural gas field, in which case it would probably contain both $H_2S$ and $CO_2$ at moderate concentrations in a range of 0.05 mole % to 8 mole %, for example; or from a thermal cracking unit producing unrefined synthetic natural gas, in which event stream 94 would likely contain a greater concentration of $CO_2$ than $H_2S$ which can range up to 30–35 molar percent $CO_2$ plus $H_2S$ (acid gases). It is anticipated that the present invention will have its greatest utility in treating gas streams containing a relatively high ratio of $CO_2$ to $H_2S$, for example, a $CO_2:H_2S$ mole ratio of greater than about 1:1, although where very high purity $H_2S$ is desired, the feed stream will usually contain a $CO_2:H_2S$ mole ratio of about 1:2 or less. For example, a synthetic gas blend containing hydrogen, ethylene, carbon dioxide, and hydrogen sulfide might exhibit a mole ratio of $CO_2:H_2S$ of about 8.8:1, while a natural gas blend might exhibit a $CO_2:H_2S$ mole ratio of 0.3:1 up to 4:1.

The alkanolamine employed in the process of the present invention preferably is selected from the group consisting methyldiethanolamine (MDEA) and n-propyldiethanolamine (PDEA). N-propyldiethanolamine is less expensive than methyldiethanolamine, but regeneration of PDEA solutions requires more energy.

Conditions in the absorber can vary widely. Preferably, contact between the first gas stream and the solution of alkanolamine is in countercurrent fashion, the solution of alkanolamine flowing in vigorous vapor contact in the absorber. The gas stream 94 is generally contacted in the contacting zone with between about 10 and about 1,000 moles of alkanolamine for each mole of $H_2S$ which it contains for good results. The alkanolamine solution employed will normally contain between about 5 and about 50 weight percent of the alkanolamine although higher or lower concentrations can be utilized if desired. Conditions in the absorber 2 will generally include a temperature within the range of from about 0° to about 100° C. and a pressure within the range of from about 0° to about 100 psig (pounds per square inch, gauge) (100-800 kilopascals,kPa).

From the absorber 2, there is withdrawn a rich solution by the conduit means 26 of the at least one alkanolamine solution which is rich in $H_2S$ and $CO_2$ from the first gas stream. This rich solution is introduced into a separation zone 16 and selectively stripped therein to produce a second gas stream 60 issuing from the separation zone 16 which contains a higher $CO_2:H_2S$ mole ratio than the first stream 94. The second gas stream 60 can be conveyed into an alkanolamine contacting zone which is the same as or different from the first zone 2. In the embodiment illustrated, after being partially condensed for reflux, a portion of the second gas stream passes through compressor 50 and is reintroduced into the zone 2, preferably at a position in the absorber at which the gas phase contains the same $CO_2:H_2S$ mole ratio as the second gas stream.

It is desirable that the second gas stream be introduced into the alkanolamine contacting zones at a point above that at which the first gas stream is introduced because $CO_2$ slippage is primarily a function of the number of absorber trays and the absorber pressure. Since pressure in the unit is constant, reducing the number of trays between the point inlet 44 at which the second stream is introduced and the purified gas stream 96 is withdrawn increases $CO_2$ slippage, where slippage is defined as the passage of $CO_2$ from the unit with the treated gas stream as percent of total $CO_2$ in feed. Another reason for introducing the second stream into an intermediate or upper section of the absorber is that high concentrations of carbon dioxide flowing upwards through the absorber tends to displace residual hydrogen sulfide from the lean solvent at the top of the absorber which can result in higher concentrations of hydrogen sulfide in the treated gas than would be expected. The efficiency of the individual trays is at least a function of the $CO_2:H_2S$ mole ratio and tray efficiency decreases as the ratio increases. This is attributed to the displacement action of carbon dioxide on the residual hydrogen sulfide in the lean solvent. The second gas stream with a high $CO_2:H_2S$ mole ratio should thus be introduced in the upper section of the absorber. This will minimize the detrimental effect of $H_2S$ displacement by $CO_2$. The result is a lessening of the detrimental effect of a high $CO_2:H_2S$ mole ratio on overall absorber $H_2S$ removal efficiency.

Generally speaking, the gas stream 94 to be treated will contain some hydrocarbon. Hydrocarbons containing greater than about 3 to 4 carbon atoms have a tendency to become dissolved in the alkanolamine solvent, and become stripped from the solvent during regeneration. This can cause operating problems, such as foaming. It is thus preferable, when hydrocarbon is present, that the gas stream to be treated contain a hydrocarbon which has from about 1 to about 3 carbon atoms. However, when the stream 44 contains heavier hydrocarbons, they may be recovered in the treated gas to increase its BTU value, rather than the acid gas, due to recycle via line 61.

Because one of the purposes of selectively stripping the alkanolamine solution is to produce a selectively stripped aqueous phase which contains a higher $H_2S:CO_2$ mole ratio than the rich solution issuing from the absorber, the selective stripping should be conducted under conditions less severe than those required to remove a major portion of the $H_2S$ from the rich alkanolamine solution. Typically, it is anticipated that the selective stripper will be operated at a pressure of between about 0 and about 40 psig, (100–450 kPa) and a temperature of from about 220° and about 260° F. (104°–127° C.).

According to another aspect of the present invention, a process comprises contacting a first gas stream containing $H_2S$, $CO_2$ and at least one hydrocarbon with a lean alkanolamine solution in a contacting zone. For example, a gas stream carried by the conduit 94 can be introduced into the absorber 2 at inlet 12 and contacted therein with lean alkanolamine solution flowing downward through the absorber from liquid inlet 8 to liquid outlet 14. The rich alkanolamine solution, which contains at least a portion of the $H_2S$ and $CO_2$ from the first gas stream is withdrawn from the contacting zone, for example, through outlet 14, and conveyed via conduit means 26 to a first stripping zone, such as the selective stripper 16 and introduced thereinto. In the selective stripping zone 16, the rich alkanolamine solution is selectively stripped to produce a second gas stream for example, 60, which issues from the stripping zone and contains a higher $CO_2:H_2S$ mole ratio than the first gas stream 94. The selectively stripped, partially regenerated, alkanolamine solution is withdrawn from the first stripping zone, for example, through outlet 21 and introduced into a second stripping zone, for example, the column 28, via conduit means 40. The selectively stripped alkanolamine solution will exhibit a higher $H_2S:CO_2$ mole ratio than the rich alkanolamine solution 26 from the contacting zone 2. In the second stripping zone, the selectively stripped solution is further stripped to produce a third gas stream, such as 90 which is rich in $H_2S$ and lean in $CO_2$. This gas stream 90 can be suitably conveyed to a Claus unit. If desired, at least a portion of the stream 90 can be fed to a second unit as shown in the drawing, i.e. be utilized as the feed stream 94 for a second unit in series with the first, to result in the production of high purity $H_2S$.

Where the feedstream 94 contains a significant concentration of hydrocarbons having greater than about 3 carbon atoms, the present process provides a recycle mechanism whereby the heavy hydrocarbons can be withdrawn from the unit via conduit 96, rather than along with the acid gases from conduit 90. The heavy hydrocarbon components can thus increase the BTU value of the treated gas, rather than possibly contaminating valuable catalyst in a Claus unit. Thus, it is desirable when practicing this embodiment of the invention that the second gas stream 61 be conveyed to the absorber 2 such as at vapor inlet 44. In any event, recycling of the stream 60 to the absorber can result in the production of increased purity $H_2S$ and is desirable for that reason.

Alkanolamine solution can be withdrawn from the second stripping zone 28 which is lean in $H_2S$ and $CO_2$ and be introduced into the absorber 2 as at inlet 8 for contacting the first gas stream 94, and conserving materials. Where these steps are taken, a treated gas stream can be withdrawn from the absorber 2, such as at conduit 96 which contains $CO_2$, at least one hydrocarbon, a minor amount of $H_2S$, and a much higher $CO_2:H_2S$ mole ratio than the first gas stream. Preferably, the gas stream 96 will exhibit a $CO_2:H_2S$ mole ratio of about 100:1 or greater. Environmental considerations arising from the combustion of such a gas stream can thus be markedly decreased.

The invention is illustrated by the following examples.

EXAMPLE I

During operation of a pilot plant unit, it was observed during regeneration of the MDEA solvent that the $CO_2$ and $H_2S$ were stripped to different degrees at various stripping conditions. For example, regenerating rich MDEA solution at different conditions in a stripper having a four inch diameter, a 20 foot length, filled with ⅜″ stainless steel Pall rings and fitted with a steam reboiler produced the following results:

TABLE I

| Stripper Kettle Temp. F.° | Stripper Pressure PSIG | Rich Solvent Wt. % $H_2S$ | Rich Solvent Wt. % $CO_2$ | Lean Solvent Wt. % $H_2S$ | Lean Solvent Wt. % $CO_2$ | Percent Removed $H_2S$ | Percent Removed $CO_2$ |
|---|---|---|---|---|---|---|---|
| 231 | 9.7 | 0.95 | 2.4 | 0.85 | 0.98 | 10.5 | 59.2 |
| 234 | 10 | 1.06 | 2.8 | 0.73 | 0.76 | 31.1 | 72.9 |
| 241 | 10 | 0.76 | 1.4 | 0.38 | 0.19 | 50.0 | 86.4 |

The runs show that the degrees to which $H_2S$ and $CO_2$ are stripped from rich MDEA solution are dependent on stripper temperature.

EXAMPLE II material balances are shown by Table III. In this example, both strippers are hypothetically operating at 10 psig and the absorber is operating at 40 psig. The lean alkanolamine solution is to comprise 30 wt. % MDEA. The hypothetical feed stream contains a higher than normal (for natural gas) $CO_2:H_2S$ mole ratio, such as might be recovered in the effluent from a pyrolysis reaction.

EXAMPLE III (Calculated)

Runs 9–13 are conducted under the conditions and with the ultimate results shown in Table IV. Calculated material balances are shown by Table V. This example shows the processing of a gas stream containing about 6.5 mole % acid gases and a $CO_2:H_2S$ mole ratio of about 4:1, and is thus representative of the processing of many sour natural gas streams. The strippers are hypothecated to be operating at 10 psig and the absorber at 40 psig with 30 wt % MDEA in the lean solvent.

EXAMPLE IV (Calculated)

This example is to demonstrate the utility of the invention for the production of high purity $H_2S$ suitable for chemical use without going through high pressure distillation. The entire operation is conducted at low pressure. In this example, both strippers and the absorber are operating at 10 psig. The lean solvent comprises about 30 wt% MDEA. The feed to the absorber comprises 100% acid gas, 30 mole % $CO_2$ and 70 mole % $H_2S$, such as might be present in a slip stream from the feed stream to a Claus Unit. A suitable feed stream could be all or a portion of the product from run 4 of Example II, for example.

Runs 14–19 are conducted under the conditions and with the ultimate results shown in Table VI. Calculated material balances are shown by Table VII. In runs 14–16, the overhead from the first stripper 61 is recycled to the absorber. In runs 17–19 the overhead is not so recycled. Under the hypothetical conditions, recycle of the stream 60 was necessary to achieve a product purity of greater than 99%.

TABLE II

| | | | CONDITIONS | | | |
|---|---|---|---|---|---|---|
| Run # | First Kettle (52) (°F.) | Second Kettle (54) (°F.) | Solvent:Acid Gas (GAL/SCF) | Solvent Circulation (GAL/100 moles feed) | $H_2S$ Product Purity (mole %) | $CO_2$ Passed (mole %) |
| 1 | 230 | 245 | 1.3843 | 12437 | 60.9 | 96.0 |
| 2 | 232 | 245 | 1.3845 | 12603 | 63.7 | 96.5 |
| 3 | 234 | 245 | 1.3846 | 12804 | 66.9 | 96.9 |
| 4 | 236 | 245 | 1.3847 | 13063 | 70.4 | 97.4 |
| 5 | 238 | 245 | 1.3849 | 13426 | 74.3 | 97.9 |
| 6 | 240 | 245 | 1.3850 | 13992 | 78.7 | 98.3 |
| 7 | 242 | 245 | 1.3851 | 15062 | 83.6 | 98.9 |
| 8 | 244 | 245 | 1.3853 | 17905 | 88.6 | 99.3 |

(Calculated)

Runs 1–8 are conducted under the conditions and with the ultimate results shown in Table II. Calculated

TABLE III

| | | MATERIAL BALANCES (moles) | | | | | | |
|---|---|---|---|---|---|---|---|---|
| | | | | | Stream No. | | | |
| Run No. | | 94 Feed Gas | 61 First Stripper OHP | 42 Lean Solvent | 96 Absorber OHP | 26 Rich Solvent | 40 1st Stripper KP | 90 2nd Stripper OHP |
| 1 | | | | | | | | |
| | $CO_2$ | 21.0 | 1.318 | 0.044 | 20.165 | 2.197 | 0.879 | 0.835 |
| | $CH_4+$ | 77.7 | 3.625 | 0 | 77.7 | 3.625 | 0 | 0 |
| | $H_2S$ | 1.3 | 0.052 | 0.078 | 0.0004 | 1.430 | 1.378 | 1.300 |

TABLE III-continued

MATERIAL BALANCES (moles)

| Run No. | | 94 Feed Gas | 61 First Stripper OHP | 42 Lean Solvent | 96 Absorber OHP | 26 Rich Solvent | 40 1st Stripper KP | 90 2nd Stripper OHP |
|---|---|---|---|---|---|---|---|---|
| | TOTAL | 100.0 | 4.995 | 0.122 | 97.865 | 7.252 | 2.257 | 2.135 |
| 2 | | | | | | | | |
| | CO$_2$ | 21.0 | 1.424 | 0.039 | 20.26 | 2.203 | 0.778 | 0.740 |
| | CH$_{4+}$ | 77.7 | 3.634 | 0 | 77.7 | 3.634 | 0 | 0 |
| | H$_2$S | 1.3 | 0.258 | 0.078 | 0.0004 | 1.635 | 1.378 | 1.300 |
| | TOTAL | 100.0 | 5.316 | 0.117 | 97.960 | 7.472 | 2.156 | 2.040 |
| 3 | | | | | | | | |
| | CO$_2$ | 21.0 | 1.531 | 0.034 | 20.356 | 2.208 | 0.677 | 0.644 |
| | CH$_{4+}$ | 77.7 | 3.644 | 0 | 77.7 | 3.644 | 0 | 0 |
| | H$_2$S | 1.3 | 0.532 | 0.078 | 0.0004 | 1.909 | 1.378 | 1.300 |
| | TOTAL | 100.0 | 5.707 | 0.112 | 98.056 | 7.761 | 2.055 | 1.944 |
| 4 | | | | | | | | |
| | CO$_2$ | 21.0 | 1.639 | 0.029 | 20.453 | 2.214 | 0.575 | 0.547 |
| | CH$_{4+}$ | 77.7 | 3.654 | 0 | 77.7 | 3.654 | 0 | 0 |
| | H$_2$S | 1.3 | 0.916 | 0.078 | 0.0004 | 2.293 | 1.378 | 1.300 |
| | TOTAL | 100.0 | 6.209 | 0.107 | 98.153 | 8.161 | 1.953 | 1.847 |
| 5 | | | | | | | | |
| | CO$_2$ | 21.0 | 1.747 | 0.023 | 20.550 | 2.220 | 0.473 | 0.450 |
| | CH$_{4+}$ | 77.7 | 3.663 | 0 | 77.7 | 3.663 | 0 | 0 |
| | H$_2$S | 1.3 | 1.494 | 0.078 | 0.0004 | 2.871 | 1.378 | 1.300 |
| | TOTAL | 100.0 | 6.904 | 0.101 | 98.250 | 8.754 | 1.851 | 1.750 |
| 6 | | | | | | | | |
| | CO$_2$ | 21.0 | 1.856 | 0.018 | 20.648 | 2.226 | 0.370 | 0.352 |
| | CH$_{4+}$ | 77.7 | 3.673 | 0 | 77.7 | 3.673 | 0 | 0 |
| | H$_2$S | 1.3 | 2.460 | 0.078 | 0.0004 | 3.837 | 1.377 | 1.300 |
| | TOTAL | 100.0 | 7.989 | 0.096 | 93.348 | 9.736 | 1.747 | 1.652 |
| 7 | | | | | | | | |
| | CO$_2$ | 21.0 | 1.965 | 0.013 | 20.746 | 2.232 | 0.267 | 0.254 |
| | CH$_{4+}$ | 77.7 | 3.683 | 0 | 77.7 | 3.683 | 0 | 0 |
| | H$_2$S | 1.3 | 4.385 | 0.078 | 0.0004 | 5.755 | 1.370 | 1.292 |
| | TOTAL | 100.0 | 10.033 | 0.091 | 98.446 | 11.670 | 1.637 | 1.546 |
| 8 | | | | | | | | |
| | CO$_2$ | 21.0 | 2.075 | 0.008 | 20.845 | 2.238 | 0.163 | 0.155 |
| | CH$_{4+}$ | 77.7 | 3.693 | 0 | 77.7 | 3.693 | 0 | 0 |
| | H$_2$S | 1.3 | 9.678 | 0.073 | 0.0004 | 10.961 | 1.284 | 1.211 |
| | TOTAL | 100.0 | 15.446 | 0.081 | 98.545 | 16.892 | 1.447 | 1.366 |

TABLE IV

CONDITIONS

| Run # | First Kettle (52) (°F.) | Second Kettle (54) (°F.) | Solvent:Acid Gas (GAL/SCF) | Solvent Circulation (GAL/100 moles feed) | H$_2$S Product Purity (mole %) | CO$_2$ Passed (mole %) |
|---|---|---|---|---|---|---|
| 9 | 230 | 245 | 1.3845 | 3737 | 87.6 | 96.5 |
| 10 | 230 | 245 | 1.3846 | 3895 | 89.1 | 96.9 |
| 11 | 230 | 245 | 1.3847 | 4111 | 90.6 | 97.4 |
| 12 | 230 | 245 | 1.3849 | 4430 | 92.1 | 97.9 |
| 13 | 230 | 245 | 1.3850 | 4951 | 93.7 | 98.3 |

TABLE V

MATERIAL BALANCES (moles)

| Run No. | | 94 Feed Gas | 61 First Stripper OHP | 42 Lean Solvent | 96 Absorber OHP | 26 Rich Solvent | 40 1st Stripper KP | 90 2nd Stripper OHP |
|---|---|---|---|---|---|---|---|---|
| 9 | | | | | | | | |
| | CO$_2$ | 5.2 | 0.353 | 0.010 | 5.017 | 0.545 | 0.193 | 0.183 |
| | CH$_{4+}$ | 93.5 | 0.900 | 0 | 93.5 | 0.900 | 0 | 0 |
| | H$_2$S | 1.3 | 0.258 | 0.078 | 0.0004 | 1.635 | 1.378 | 1.300 |
| | TOTAL | 100.0 | 1.511 | 0.088 | 98.517 | 3.080 | 1.571 | 1.483 |
| 10 | | | | | | | | |
| | CO$_2$ | 5.2 | 0.379 | 0.008 | 5.041 | 0.547 | 0.168 | 0.159 |
| | CH$_{4+}$ | 93.5 | 0.902 | 0 | 93.5 | 0.902 | 0 | 0 |
| | H$_2$S | 1.3 | 0.532 | 0.078 | 0.0004 | 1.909 | 1.378 | 1.300 |
| | TOTAL | 100.0 | 1.813 | 0.086 | 98.541 | 3.358 | 1.545 | 1.459 |
| 11 | | | | | | | | |
| | CO$_2$ | 5.2 | 0.406 | 0.007 | 5.065 | 0.548 | 0.142 | 0.135 |
| | CH$_{4+}$ | 93.5 | 0.905 | 0 | 93.5 | 0.905 | 0 | 0 |
| | H$_2$S | 1.3 | 0.916 | 0.078 | 0.0004 | 2.293 | 1.378 | 1.300 |
| | TOTAL | 100.0 | 2.227 | 0.085 | 98.565 | 3.746 | 1.520 | 1.435 |
| 12 | | | | | | | | |
| | CO$_2$ | 5.2 | 0.433 | 0.006 | 5.089 | 0.550 | 0.117 | 0.111 |
| | CH$_{4+}$ | 93.5 | 0.907 | 0 | 93.5 | 0.907 | 0 | 0 |
| | H$_2$S | 1.3 | 1.494 | 0.078 | 0.0004 | 2.871 | 1.378 | 1.300 |
| | TOTAL | 100.0 | 2.834 | 0.084 | 98.589 | 4.328 | 1.495 | 1.411 |

TABLE V-continued

MATERIAL BALANCES (moles)

| Run No. | | 94 Feed Gas | 61 First Stripper OHP | 42 Lean Solvent | 96 Absorber OHP | 26 Rich Solvent | 40 1st Stripper KP | 90 2nd Stripper OHP |
|---|---|---|---|---|---|---|---|---|
| 13 | $CO_2$ | 5.2 | 0.460 | 0.005 | 5.113 | 0.551 | 0.092 | 0.087 |
| | $CH_{4+}$ | 93.5 | 0.910 | 0 | 93.5 | 0.910 | 0 | 0 |
| | $H_2S$ | 1.3 | 2.459 | 0.078 | 0.0004 | 3.836 | 1.377 | 1.300 |
| | TOTAL | 100.0 | 3.829 | 0.083 | 98.613 | 5.297 | 1.469 | 1.387 |

TABLE VI

CONDITIONS

| Run # | First Kettle (52) (°F.) | Second Kettle (54) (°F.) | Solvent:Acid Gas (GAL/SCF) | Solvent Circulation (GAL/100 moles feed) | $H_2S$ Product Purity (mole %) | $CO_2$ Passed (mole %) |
|---|---|---|---|---|---|---|
| 14 | 235 | 245 | 1.3854 | 53,252 | 98.80 | 97.17 |
| 15 | 240 | 245 | 1.3854 | 89,273 | 99.29 | 98.33 |
| 16 | 244 | 245 | 1.3854 | 251,417 | 99.68 | 99.27 |
| 17 | 235 | 245 | 1.3854 | 52,584 | 98.28 | 90.33 |
| 18 | 240 | 245 | 1.3854 | 52,584 | 98.12 | 90.33 |
| 19 | 244 | 245 | 1.3854 | 52,584 | 97.47 | 90.33 |

TABLE VII

MATERIAL BALANCES (moles)

| Run No. | | 94 Feed Gas | 60 First Stripper OHP | 42 Lean Solvent | 96 Absorber OHP | 26 Rich Solvent | 40 1st Stripper KP | 90 2nd Stripper OHP |
|---|---|---|---|---|---|---|---|---|
| 14 | $CO_2$ | 30 | 2.27 | 0.044 | 29.15 | 3.16 | 0.896 | 0.85 |
| | $H_2S$ | 70 | 38.03 | 4.205 | 0.0001 | 112.24 | 74.205 | 70.0 |
| | TOTAL | 100 | 40.30 | 4.249 | 29.1501 | 115.40 | 75.101 | 70.85 |
| 15 | $CO_2$ | 30 | 2.65 | 0.026 | 29.50 | 3.18 | 0.530 | 0.500 |
| | $H_2S$ | 70 | 132.55 | 4.205 | 0.0001 | 206.76 | 74.206 | 70.0 |
| | TOTAL | 100 | 135.20 | 4.231 | 29.5001 | 209.94 | 74.736 | 70.50 |
| 16 | $CO_2$ | 30 | 2.96 | 0.012 | 29.78 | 3.20 | 0.233 | 0.221 |
| | $H_2S$ | 70 | 559.43 | 4.205 | 0.0001 | 633.64 | 74.205 | 70.0 |
| | TOTAL | 100 | 562.39 | 4.217 | 29.7801 | 636.84 | 74.438 | 70.221 |
| 17 | $CO_2$ | 30 | 2.11 | 0.04 | 27.1 | 2.94 | 0.83 | 0.79 |
| | $H_2S$ | 70 | 24.64 | 2.72 | .0001 | 72.72 | 48.08 | 45.36 |
| | TOTAL | 100 | 26.75 | 2.76 | 27.1001 | 75.66 | 48.91 | 46.15 |
| 18 | $CO_2$ | 30 | 2.44 | 0.02 | 27.10 | 2.92 | 0.49 | .46 |
| | $H_2S$ | 70 | 45.81 | 1.45 | .0001 | 71.45 | 25.64 | 24.19 |
| | TOTAL | 100 | 48.25 | 1.47 | 27.1001 | 74.37 | 26.13 | 24.65 |
| 19 | $CO_2$ | 30 | 2.70 | 0.01 | 27.10 | 2.91 | 0.21 | .20 |
| | $H_2S$ | 70 | 62.22 | 0.47 | .0001 | 70.47 | 8.25 | 7.78 |
| | TOTAL | 100 | 64.92 | 0.48 | 27.1001 | 73.38 | 8.46 | 7.98 |

That which is claimed is:

1. A process comprising:
   (a) contacting a first gas stream containing $CO_2$, $H_2S$ and at least one hydrocarbon with a solution of at least one alkanolamine in a contacting zone;
   (b) withdrawing from the contacting zone a rich solution of at least one alkanolamine which is rich in $H_2S$ and $CO_2$ from the first gas stream;
   (c) introducing the rich solution into a separation zone;
   (d) selectively stripping the rich solution in the separation zone to produce a second gas stream issuing from the separation zone which contains a higher $CO_2:H_2S$ mole ratio than the first stream; and
   (e) conveying the second gas stream into an alkanolamine contacting zone.

2. A process as in claim 1 wherein the at least one hydrocarbon to be treated in the first gas stream contains from one to about 3 carbon atoms and wherein the alkanolamine contacting zone to which the second gas stream is conveyed is the same zone as the contacting zone in which the first gas stream was contacted with the solution of at least one alkanolamine.

3. A process as in claim 2 wherein the at least one alkanolamine is selected from the group consisting of methyldiethanolamine and n-propyldiethanolamine.

4. A process as in claim 3 wherein the first gas stream is contacted in the contacting zone with between about 10 and 1000 moles of alkanolamine for each mole of $H_2S$ which it contains.

5. A process as in claim 4 wherein the alkanolamine solution contains between about 5 and about 50 weight percent of the alkanolamine.

6. A process as in claim 5 wherein conditions in the contacting zone include a temperature within the range of 0°–100° C. and a pressure within the range of from about 0 to about 100 pounds per square inch, gauge.

7. A process as in claims 6 further comprising withdrawing a selectively stripped alkanolamine solution from the separation zone which exhibits a higher $H_2S:CO_2$ mole ratio than the rich alkanolamine solution withdrawn from the contacting zone.

8. A process as in claim 7 wherein the alkanolamine comprises methyldiethanolamine.

9. A process comprising:
(a) contacting a first gas stream containing $H_2S$, $CO_2$ and at least one hydrocarbon with a lean alkanolamine solution in a contacting zone;
(b) withdrawing a rich alkanolamine solution from the contacting zone which contains at least a portion of the $H_2S$ and $CO_2$ from the first gas stream;
(c) introducing the rich alkanolamine solution into a first stripping zone;
(d) selectively stripping the rich alkanolamine solution in the first stripping zone to produce a second gas stream issuing from the stripping zone which contains a higher $CO_2:H_2S$ mole ratio than the first gas stream;
(e) withdrawing a selectively stripped alkanolamine solution from the first stripping zone, said selectively stripped alkanolamine solution containing a higher $H_2S:CO_2$ mole ratio than the rich alkanolamine solution from the contacting zone;
(f) introducing the selectively stripped solution into a second stripping zone; and
(g) stripping the selectively stripped solution to produce a third gas stream which is rich in $H_2S$ and lean in $CO_2$.

10. A process as in claim 9 further comprising withdrawing an alkanolamine solution from the second stripping zone which is lean in $H_2S$ and $CO_2$ and introducing the withdrawn lean solution into the contacting zone for contacting the first gas stream.

11. A process as in claim 10 further comprising introducing the second gas stream into the contacting zone for contact with the lean alkanolamine solution.

12. A process as in claim 11 further comprising withdrawing a fourth gas stream from the contacting zone containing $CO_2$, at least one hydrocarbon, and a minor amount of $H_2S$, said fourth gas stream having a higher $CO_2:H_2S$ mole ratio than the first gas stream.

13. A process as in claim 12 wherein the alkanolamine is selected from the group consisting of methyldiethanolamine, n-propyldiethanolamine and mixtures thereof.

14. A process as in claim 13 wherein the at least one hydrocarbon in the first gas stream contains from one to about 3 carbon atoms.

15. A process as in claim 14 wherein the first gas stream further contains olefins and molecular hydrogen.

16. A process as in claim 14 wherein the alkanolamine solution comprises from about a 10 to about a 30 weight percent solution of methyldiethanolamine.

* * * * *